(12) United States Patent
Jayasundera et al.

(10) Patent No.: US 9,757,023 B2
(45) Date of Patent: Sep. 12, 2017

(54) OPTIC DISC DETECTION IN RETINAL AUTOFLUORESCENCE IMAGES

(71) Applicant: THE REGENTS OF THE UNIVERSITY OF MICHIGAN, Ann Arbor, MI (US)

(72) Inventors: Kanishka T. Jayasundera, Ann Arbor, MI (US); Matthew K. Johnson-Roberson, Chestnut Hill, MA (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/165,400

(22) Filed: May 26, 2016

(65) Prior Publication Data

US 2016/0345819 A1 Dec. 1, 2016

Related U.S. Application Data

(60) Provisional application No. 62/167,224, filed on May 27, 2015, provisional application No. 62/167,413, filed on May 28, 2015.

(51) Int. Cl.
*A61B 3/14* (2006.01)
*A61B 3/00* (2006.01)
*A61B 3/12* (2006.01)

(52) U.S. Cl.
CPC .......... *A61B 3/0025* (2013.01); *A61B 3/1241* (2013.01); *A61B 3/14* (2013.01); *G06T 2207/30041* (2013.01)

(58) Field of Classification Search
USPC ................................................ 351/200–246
See application file for complete search history.

(56) References Cited

U.S. PATENT DOCUMENTS 5,692,220 A 11/1997 Diamond et al.
5,868,134 A 2/1999 Sugiyama et al.
(Continued)

FOREIGN PATENT DOCUMENTS

WO WO-2009/148067 A1 12/2009
WO WO-2013/058907 A1 4/2013

OTHER PUBLICATIONS

A randomized, placebo-controlled, clinical trial of high-dose supplementation with vitamins C and E and beta carotene for age-related cataract and vision loss: AREDS report No. 9. Arch Ophthalmol. Oct. 2001;119(10):1439-1452.
(Continued)

*Primary Examiner* — Mohammed Hasan
(74) *Attorney, Agent, or Firm* — Marshall, Gerstein & Borun LLP; Randall G. Rueth (57) ABSTRACT

The invention relates to methods and systems for automatically detecting an optic disc in a retinal fundus autofluorescence image. A monochromatic image of a retina is obtained by stimulated autofluorescence. The image is processed using filters and machine learning to identify blood vessel segments and to identify pixels as possible optic disc pixels. The possible optic disc pixels are grouped into clusters, and a best fit circle (or portion thereof lying within the image) is fitted to each cluster. The circle may be enlarged to improve image contrast at the circumference of the circle. Blood vessel segments that intersect the circle are identified, and metrics are derived from such intersecting blood vessel segments. These metrics are assessed by machine learning processes to determine the probability that each cluster contains the optic disc, and the contours of the optic disc are further determined by analysis of the possible optic disc pixels.

20 Claims, 5 Drawing Sheets

(56) References Cited

U.S. PATENT DOCUMENTS

| | | | |
|---|---|---|---|
| 6,053,865 A | 4/2000 | Sugiyama et al. | |
| 6,104,828 A | 8/2000 | Shioiri | |
| 6,698,885 B2 | 3/2004 | Berger et al. | |
| 7,147,329 B2 | 12/2006 | Berger et al. | |
| 7,283,653 B2 | 10/2007 | Zahlmann et al. | |
| 7,474,775 B2 | 1/2009 | Abramoff et al. | |
| 7,488,071 B2 | 2/2009 | Ogawa et al. | |
| 7,512,436 B2 | 3/2009 | Petty et al. | |
| 7,524,061 B2 | 4/2009 | Yan et al. | |
| 7,568,800 B2 | 8/2009 | Mihashi et al. | |
| 7,583,827 B2 | 9/2009 | Hansen et al. | |
| 7,856,135 B1 | 12/2010 | Bernardes | |
| 8,041,091 B2 | 10/2011 | de Oliveira e Ramos et al. | |
| 8,218,838 B2 | 7/2012 | Karnowski et al. | |
| 8,351,669 B2* | 1/2013 | Gonzalez | G06K 9/00604 351/206 |
| 8,503,749 B2 | 8/2013 | Tobin et al. | |
| 8,687,862 B2 | 4/2014 | Hsu et al. | |
| 8,705,826 B2 | 4/2014 | Liu et al. | |
| 9,228,233 B2 | 1/2016 | Kennedy et al. | |
| 2004/0115646 A1 | 6/2004 | Finkelstein | |
| 2004/0122709 A1 | 6/2004 | Avinash et al. | |
| 2005/0094099 A1 | 5/2005 | Newman et al. | |
| 2005/0171974 A1 | 8/2005 | Doering | |
| 2007/0002275 A1 | 1/2007 | Yan et al. | |
| 2007/0025606 A1 | 2/2007 | Gholap et al. | |
| 2007/0188705 A1 | 8/2007 | Tajima et al. | |
| 2008/0100612 A1 | 5/2008 | Dastmalchi et al. | |
| 2008/0273174 A1 | 11/2008 | Tan | |
| 2009/0143685 A1 | 6/2009 | Elner et al. | |
| 2010/0302507 A1 | 12/2010 | Desgroseilliers et al. | |
| 2011/0058718 A1 | 3/2011 | Nakajima et al. | |
| 2011/0160562 A1 | 6/2011 | de Oliveira E Ramos et al. | |
| 2011/0299034 A1 | 12/2011 | Walsh et al. | |
| 2012/0102405 A1 | 4/2012 | Zuckerman et al. | |
| 2012/0177262 A1 | 7/2012 | Bhuiyan | |
| 2012/0237096 A1 | 9/2012 | Tobin et al. | |
| 2012/0257164 A1 | 10/2012 | Zee et al. | |
| 2012/0300998 A1 | 11/2012 | Ioudovski et al. | |
| 2013/0184161 A1 | 7/2013 | Kingsmore et al. | |
| 2013/0208245 A1 | 8/2013 | Campbell | |
| 2014/0270444 A1 | 9/2014 | Yang et al. | |
| 2015/0029464 A1 | 1/2015 | Jayasundera et al. | |
| 2015/0088870 A1 | 3/2015 | Jayasundera et al. | |
| 2017/0112372 A1* | 4/2017 | Chakravorty | A61B 3/0025 |

OTHER PUBLICATIONS

Sinthanayothin et al., Automated localisation of the optic disc, fovea, and retinal blood vessels from digital colour fundus images, Br. J. Opthalmol., 83:902-10 (1999).

Bearelly et al., Fundus autofluorescence imaging in age-related macular degeneration and geographic atrophy. Adv Exp Med Biol. 2010;664:395-402.

Bearelly et al. Use of fundus autofluorescence images to predict geographic atrophy progression. Retina. Jan. 2011;31(1):81-86.

Bressler et al., Interobserver and intraobserver reliability in the clinical classification of drusen. Retina. 1988;8(2)102-108.

Chan et al., Active contours without edges for vector-valued images, J. Visual Communication and Image Representation, 11(2):130-41 (2000).

Chylack et al. The Lens Opacities Classification System III. The Longitudinal Study of Cataract Study Group. Arch Ophthalmol. Jun. 1993;111(6):831-836.

Cree et al., The preprocessing of retinal images for the detection of fluorescein leakage, Physics in Medicine and Biology, 44(1):293-308 (1999).

Davis et al. The Age-Related Eye Disease Study severity scale for age-related macular degeneration: AREDS Report No. 17. Arch Ophthalmol. Nov. 2005;123(11):1484-1498.

Delori et al. Quantitative measurements of autofluorescence with the scanning laser ophthalmoscope. Invest Ophthalmol Vis Sci. 2011;52(13):9379-9390.

Delori et al., Autofluorescence distribution associated with drusen in age-related macular degeneration. Invest Ophthalmol Vis Sci. Feb. 2000;41(2):496-504.

Dimitrov et al., Measuring rod and cone dynamics in age-related maculopathy. Invest Ophthalmol Vis Sci. Jan. 2008;49(1):55-65.

Dimitrov et al. Visual function tests as potential biomarkers in age-related macular degeneration. Invest Ophthalmol Vis Sci. 2011:52(13):9457-9469.

Einbock et al., Changes in fundus autofluorescence in patients with age-related maculopathy. Correlation to visual function: a prospective study. Graefes Arch Clin Exp Ophthalmol. Apr. 2005;243(4):300-305.

Fan et al., Liblinear: A library for large linear classification, J. Machine Learning Res., vol. 9 pp. 1871-1874 (2008).

Foracchia et al., Luminosity and contrast normalization in retinal images, Medical Image Analysis, 9(3):179-90 (2005).

Friedman et al., Prevalence of agerelated macular degeneration in the United States, Arch. Opthalmol., 122(4):564-72 (2004).

Gess et al., Imaging in neovascular age-related macular degeneration. Semin Ophthalmol. May 2011:26(3):225-233.

Gobel et al., Imaging geographic atrophy in age-related macular degeneration. Ophthalmologica. 2011;226(4):182-190.

Holz et al., Fundus autofluorescence and development of geographic atrophy in age-related macular degeneration. Invest Ophthalmol Vis Sci. Apr. 2001;42(5):1051-1056.

Hu et al., Multimodal retinal vessel segmentation from spectral-domain optical coherence tomography and fundus photography, IEEE Trans Med. Imaging, 31(10):1-28 (2012).

Hwang et al., Predictive value of fundus autofluorescence for development of geographic atrophy in age-related macular degeneration. Invest Ophthalmol Vis Sci. Jun. 2006;47(6):2655-2661.

International Search Report and Written Opinion for corresponding International Patent Application No. PCT/US2014/048222, dated Nov. 13, 2014.

International Search Report and Written Opinion in corresponding International Application No. PCT/US2014/056891, dated Dec. 23, 2014.

Jager et al., Age-related macular degeneration. N Engl J Med. Jun. 12 2008;358(24):2606-2617.

Karadimas et al., Fundus autofluorescence imaging in serous and drusenoid pigment epithelial detachments associated with age-related macular degeneration. Am J Ophthalmol. Dec. 2005;140(6):1163-1165.

Kharghanian et al., Retinal blood vessel segmentation using Gabor wavelet and line operator, IEEE Trans. Biomedical Engineering, (2012).

Laliberte et al., Three-Dimensional Visualization of Human Fundus From a Sequence of Angiograms, SPIE Conference Proceeding (Mar. 22, 2005).

Lalonde et al., Fast and robust optic disc detection using pyramidal decomposition and hausdorff-based template matching, IEEE Trans. Medical Imaging, 20(11):1193-200 (2001).

Hoover et al., Locating blood vessels in retinal images by piecewise threshold probing of a matched filter response, IEEE Trans Medical Imaging, 19(3):203-10 (2000).

Lu et al., Automatic optic disc detection from retinal images by a line operator, IEEE Trans. Biomedical Engineering, 58(1):88-94 (2011).

Nixon, Preoperative cataract grading by Scheimpflug imaging and effect on operative fluidics and phacoemulsification energy. J Cataract Refract Surg. Feb. 2010;36(2):242-246.

Derpanis, Overview of the RANSAC Algorithm, Version 1.2 (May 13, 2010).

Park et al., Locating the optic disc in retinal images, Computer Graphics, Imaging and Visualisation, 20006 International Conference (IEEE) pp. 141-145 (2006).

Querques et al., Microperimetric Correlations of Autofluorescence and Optical Coherence Tomography Imaging in Dry Age-Related Macular Degeneration. Am J Ophthalmol. Feb. 7, 2012.

Gonzales et al., Digital Image Processing Using MATLAB. Prentice-Hall, Inc., Upper Saddle River, NJ, USA (2003).

(56) References Cited

OTHER PUBLICATIONS

RetmarkerAMD Research. (2010). Retrieved Jun. 18, 2013 from Critical Health, SA Website: <http://www.retmarker.com/docs/RetmarkerAMDResearch.pdf>.

RetmarkerC Automatic Detection of Retinal Changes. (n.d.). Retrieved Jun. 18, 2013 from Critical Health, SA Website: <http://www.retmarker.com/docs/RetmarkerC.pdf>.

RetmarkerDR Biomarker for Diabetic Retinopathy Progression. (2009). Retrieved Jun. 18, 2013 from Critical Health, SA Website: <http://www.retmarker.com/docs/RetmarkerDR.pdf>.

Richter-Mueksch et al., The influence of cortical, nuclear, subcortical posterior, and mixed cataract on the results of microperimetry. Eye (Lond). Oct. 2011;25(10):1317-1321.

Schachar et al., Quantification of Fundus Autofluorescence to Detect Disease Severity in Nonexudative Age-Related Macular Degeneration. Jama Ophthalmol, Jun. 20, 2013, E1-E7.

Schmitz-Valckenberg et al., Fundus autofluorescence imaging: review and perspectives. Retina. Mar. 2008;28(3):385-409.

Scholl et al. Inter—and intra-observer variability in grading lesions of age-related maculopathy and macular degeneration. Graefes Arch Clin Exp Ophthalmol. Jan. 2003;241(1):39-47.

Mendonca et al., Segmentation of retinal blood vessels by combining the detection of centerlines and morphological reconstruction, IEEE Trans Medical Imaging, 25(9):1200-13 (2006).

Smith et al., Autofluorescence characteristics of early, atrophic, and high-risk fellow eyes in age-related macular degeneration. Invest Ophthalmol Vis Sci. Dec. 2006;47(12):5495-5504.

Smith et al., Autofluorescence characteristics of normal foveas and reconstruction of foveal autofluorescence from limited data subsets. Invest Ophthalmol Vis Sci. Aug. 2005;46(8):2940-2946.

Smith et al., Photographic patterns in macular images: representation by a mathematical model. J Biomed Opt. Jan.-Feb. 2004;9(1):162-172.

Smith et al. Dynamic soft drusen remodelling in age-related macular degeneration. Br J Ophthalmol. Dec. 2010;94(12):1618-1623.

Sohrab et al., Imaging characteristics of dry age-related macular degeneration. Semin Ophthalmol. May 2011;26(3):156-166.

Sunness et al., Measuring geographic atrophy in advanced age-related macular degeneration. Invest Ophthalmol Vis Sci. Jul. 1999;40(8):1761-1769.

Taubin, Estimation of planar curves, surfaces, and nonplanar space curves defined by implicit equations with applications to edge and range image segmentation, IEEE Trans. Pattern Analysis and Machine Intelligence, 13(11):1115-38 (1991).

Telea et al., An augmented fast marching method for computing skeletons and centerlines, Proceedings of the Symposium on Data Visualisation, Eurographics Association, pp. 251—ff (2002).

The Age-Related Eye Disease Study system for classifying age-related macular degeneration from stereoscopic color fundus photographs: the Age-Related Eye Disease Study Report No. 6. Am J Ophthalmol. Nov. 2001;132(5):668-681.

Tobin et al., Detection of anatomic structures in human retinal imagery, IEEE Trans. Medical Imaging, 26(12):1729-39 (2007).

Youssif et al., Optic disc detection from normalized digital fundus images by means of a vessels' direction matched filter, IEE Trans. Medical Imaging, 27(1):11-8 (2008).

\* cited by examiner

OPTIC DISC DETECTION IN RETINAL AUTOFLUORESCENCE IMAGES

CROSS-REFERENCE TO RELATED APPLICATIONS

This application claims the benefit of U.S. Provisional Application No. 62/167,413, filed on May 28, 2015, and U.S. Provisional Application No. 62/167,224, filed on May 27, 2015, the entirety of which are incorporated by reference herein.

TECHNICAL FIELD

The present disclosure generally relates to automatic detection of optic discs in ocular fundus autofluorescence images, which has particular use in identifying diseases of the eye.

BACKGROUND

The human retina is a thin layer of neural tissue at the back of the eye that transforms light into electrical signals which are sent to the brain. The retina can be divided into distinct regions related to their visual function. These regions include the macula (where the majority of photoreceptor cells responsible for high-acuity color vision lie) pericentral and peripheral retina (which includes everything outside the macula and is responsible for our peripheral vision). The retina peripheral to the macula includes a non-photosensitive structure known as the optic disc. Automatic optic disc detection in retinal images is an important task due to the optic disc's usefulness as a landmark for further retinal image processing along with the usefulness of its appearance as an indicator for some diseases of the eye. In the case of the former, establishing the optic disc as a landmark allows for the creation of a coordinate system that may be used to better assess the position of disease features or help one detect other anatomical structures of the retina, such as the fovea. The fovea is a region within the center of the macula that includes the vast majority of cone cells and is responsible for nearly all of our high acuity color vision. Because the macula is crucial for normal vision, it is important that eye care specialists be able to closely monitor structural changes in this region that can lead to irreparable cell death.

To visually observe and monitor the structure of the retina, physicians currently rely on various medical imaging techniques, one of which being fundus autofluorescence (AF) photography. The word fundus refers to the surface of an organ opposite its opening, and in this case refers to the retina. AF imaging relies on the inherent fluorescence of proteins and other molecules produced by cells in the retina, particularly lipofuscin. These molecules can be excited by striking them with light of certain wavelengths, causing the molecules to reflect light of a longer wavelength back to the camera. This reflected light can be captured and turned into an electrical signal to be processed and displayed as a monochromatic image of the retina. In such images areas exhibiting excessive accumulation of metabolic products such as lipofuscin appear brighter than surrounding tissue, and areas with decreased accumulation appear darker. Areas where cells have died completely in a process known as atrophy appear black. The observable image feature is known as geographic atrophy and may appear similar to the optic disc in AF images.

While methods for detecting the optic disc in color fundus images of the retina exist, there are currently none that address the challenges of detecting the optic disc in monochromatic AF images. Additionally, existing methods fail to address the challenges introduced by the optic disc being in the presence of geographic atrophy. For example, geographic atrophy may occur as a disease feature characteristic of dry Age Related Macular Degeneration (AMD), which afflicts millions of people. AMD is a disease that can be easily observed using AF imaging. Although not yet developed, automatic detection of the geographic atrophy present in AF images has the potential to allow physicians to easily monitor the growth of these regions of atrophy if they can be distinguished from optic discs. Therefore, the detection and exclusion of the optic disc from atrophy segmentation is desirable, but no methods currently exist to do so. In addition to differentiating the optic disc from atrophy or other similar regions in AF images, optic disc detection is also hampered by the narrow angle (e.g. 30°) field of view in AF images focused on the macula. Such narrow field of view frequently leaves the optic disc partially beyond the edge of the image, thereby limiting use of geometric or template-matching approaches.

Moreover, the methods for identifying optic discs in color fundus images use some variation of a filtering or template-matching techniques based on either vessel geometry or the geometry of the optic disc itself. These approaches cannot be applied to AF images because they rely upon correlations with the dense structure of intersecting vessels at the center of the optic disc and/or a clear distinction between the optic disc and any other structures present. Unlike color images, monochromatic AF images do not usually produce visible details sufficient to distinguish the many vessels within the optic disc. In the case of template matching, which involves calculating correlations to a well demarcated circular shape, the presence of disease may result in false positives in AF images featuring AMD due to the strong similarity to the appearance of atrophy. Atrophy also often produces smooth, round, very dark and well demarcated regions in AF images. This also limits the usefulness of other methods that use of edge detection or thresholding based on intensity or image variation at the optic disc boundary or central region.

SUMMARY

According to some aspects disclosed herein, a method, system, or computer-readable medium storing instructions for automatically identifying optic discs may comprise: receiving a fundus autofluorescence image of an ocular fundus; identifying blood vessel segments within the received image; classifying a plurality of pixels of the image as possible optic disc pixels; identifying a group of possible optic disc pixels; fitting at least a portion of a circle to the group of possible optic disc pixels; identifying each of the blood vessel segments that intersects the circle; weighting each intersecting blood vessel segment based upon its alignment to the radial direction of the circle at the point of intersection; calculating a measure of radial vessel density based upon the weighted blood vessel segments and the length of the portion of the circle; determining the circle contains the optic disc based at least in part upon the measure of radial vessel density; and determining the boundaries of the determined optic disc based at least in part upon the possible optic disc pixels within the circle. In some embodiments, a plurality of groups of possible optic disc pixels may be identified, and a measure of radial vessel density may be calculated for each identified group. Based at least in part upon the plurality of measures of radial vessel density, only one of the groups may be determined to contain the optic disc.

To obtain the fundus autofluorescence image, a retinal imaging device such as a specialized camera may be used. In such embodiments, a light source of the camera or other retinal imaging device may transmit a stimulating light into the retina, causing a portion of the retinal to autofluoresce. An optical sensor array of the camera may then receive autofluorescence from the ocular fundus, and a processor of the camera may process the received autofluorescence into a monochromatic digital image. The monochromatic image generated or received may lack sufficient detail to distinguish blood vessels within the optic disc. In some embodiments, therefore, determining the circle fitted to the group of possible optic disc pixels contains the optic disc will not include analyzing one or more aspects of the structure of blood vessels within the optic disc.

In some embodiments, fitting the portion of a circle to the group of possible optic disc pixels may include determining a best fit circle, then determining an expanded circle concentric with the best fit circle that has a radius larger than the radius of the best fit circle. Where a portion of the expanded circle may lie beyond the area of the received image, the portion of the expanded circle that lies within the received image may be determined. In certain preferred embodiments, the radius of the expanded circle may be between 25% and 50% larger than the radius of the best fit circle. In a particularly preferred embodiment, the radius of the expanded circle may be approximately one-third larger than the radius of the best fit circle. Additionally, or alternatively, fitting the circle to the group of possible optic disc pixels may include using a curve estimation algorithm to generate one or more potential circles around the perimeter of the group of possible optic disc pixels. Measures of goodness of fit may be determined for each of the one or more potential circles, and the potential circle with the best measure of the goodness of fit may be selected.

In some embodiments, determining the circle containing the optic disc may involve machine learning algorithms or techniques to determine a probability that the circle contains the optic disc. The circle may then be determined to contain the optic disc when the determined probability exceeds a threshold level. Additionally, or alternatively, determining the circle containing the optic disc may further be based upon additional measures derived from the received image. Such measures may include a measure of alignment of the intersecting blood vessel segments, a measure of the density of blood vessel crossings, or a measure of normalized size of the group of possible optic disc pixels. The measure of alignment of the intersecting blood vessel segments may be a measure of the average alignment to the radial direction of the circle at the point of intersection of each intersecting blood vessel segment. The measure of the density of blood vessel crossings may be a measure of the number of intersecting blood vessel segments relative to the length of the circumference of the portion of the circle within the image. The measure of normalized size of the group of possible optic disc pixels may be a measure of the radius of the circle divided by an average thickness of blood vessels present in the image.

In various embodiments, the method, system, or medium may further include: generating an illumination corrected image by correcting uneven illumination and contrast in the received image; generating a texture image by filtering the received image using filters that emphasize blood vessels; determining corresponding regions of each of the received image, the illumination corrected image, and the texture image; and generating a combined image comprising multi-dimensional pixels by combining the received image, the illumination corrected image, and the texture image. Each of the corresponding regions of the received image, the illumination corrected image, and the texture image represents the same area of the fundus in the received image. Specifically, the corresponding regions each contain the portion of the circle that is within each of the received image, the illumination corrected image, and the texture image. In such embodiments, determining the boundaries of the determined optic disc may include determining the boundaries based upon the multi-dimensional pixels of the combined image.

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112(f).

Disclosed herein are methods, systems, and media for robustly detecting and segmenting optic discs in retinal images. These may utilize supervised learning on a combination of region-based features that can differentiate the optic disc from atrophy in the macula. The optic disc may be detected even in macular centered autoflourescence images and when the optic disc lies partially off the image frame (i.e., partially outside the image area). This is achieved by analysis of the blood vessels near the optic disc, rather than within the optic disc. In some embodiments, the features indicating the presence, density, direction, and thickness of blood vessels are particularly used. The shape of the optic disc may also be determined using the same features in some embodiments. Such features may be analyzed for each of several clusters of pixels that may be identified as possibly being associated with the optic disc. Unlike other methods of identifying optic discs, those described herein can detect optic discs regardless of size or location within the retinal image. Even optic discs lying partially outside the image area can be detected.

System Overview

Figure 1:
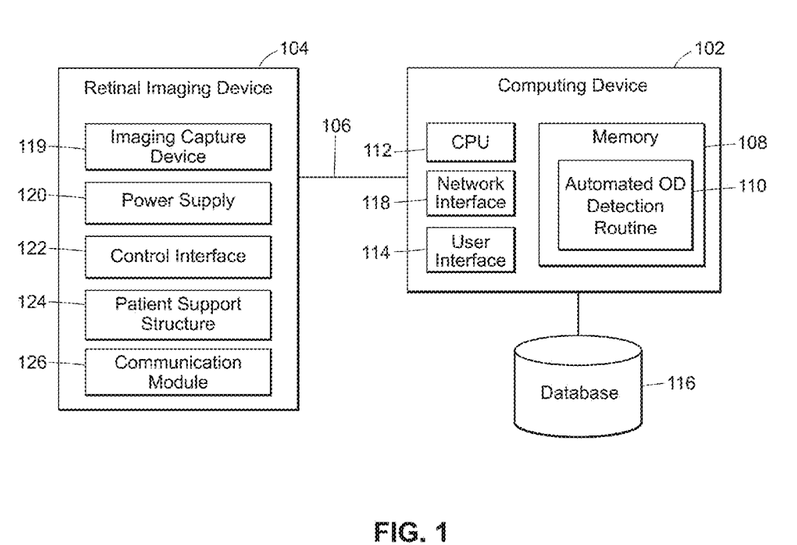
FIG. 1 illustrates a block diagram of an exemplary system for automatically detecting optic discs in fundus autofluorescence images in accordance with the embodiments described herein.
Figure 2:
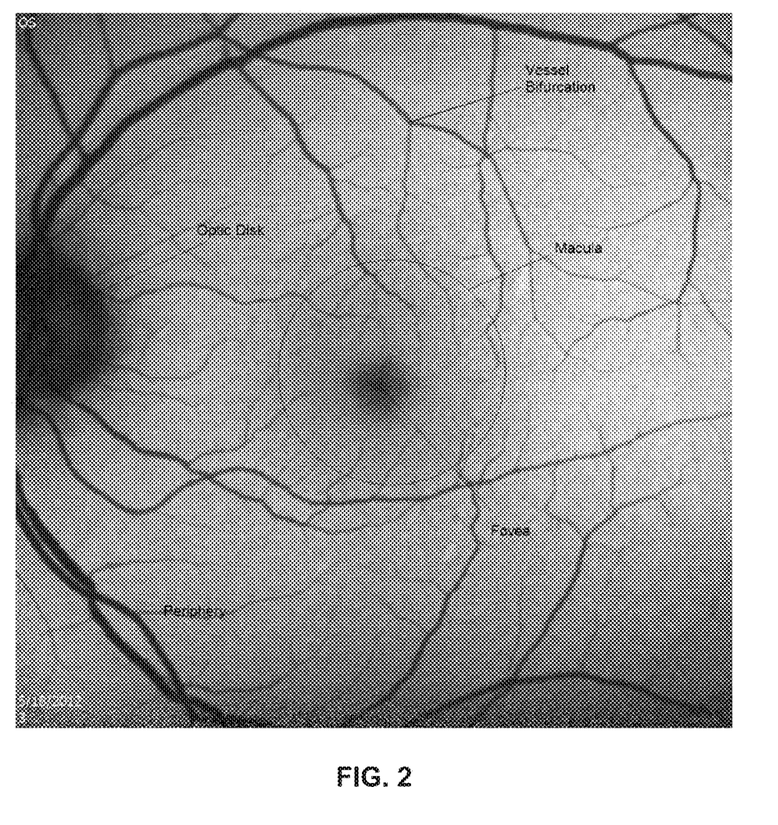
FIG. 2 illustrates an exemplary fundus autofluorescence image of a retina showing key features thereof.

FIG. 1 illustrates an example system 100 in which a computing device 102 may automatically detect optic discs in fundus autofluorescence ("AF") images from a retinal imaging device 104. FIG. 2 illustrates an exemplary AF image that may be generated by a retinal imaging device 104, showing several key features of the retina. The retina can be divided into distinct regions related to their visual function. These regions are the macula, where the majority of cones lie (photoreceptor cells responsible for central, high acuity color vision), and the periphery, which includes everything outside the macula. The periphery is responsible for our peripheral vision via another type of specialized photoreceptor cells known as rods. The periphery also includes a non-photosensitive structure known as the optic disc, where the optic nerve begins and where the major blood vessels supplying the retina enter the eye. Blood vessels and vessel bifurcations are also visible within the image. Within the center of the macula is another region known as the fovea, which includes the vast majority of cone cells. Therefore, the fovea is responsible for nearly all of our high acuity color vision. Because the macula is invaluable to normal vision, it is of the upmost importance for eye care specialists to closely monitor structural changes in this region caused by dysfunction that can lead to irreparable cell death.

Returning to FIG. 1, the exemplary retinal imaging device 104 includes an image capture device 119, a power supply 120, a control interface 122, a patient support structure 124, and a communication module 126, but the retinal imaging device 104 may be any type of device capable of generating an image of an ocular fundus based upon autofluorescence. Thus, the image capture device 119 may include a specialized or general purpose digital camera, which may be equipped with a light source that generates coherent or incoherent light to stimulate autofluorescence. In some embodiments, the camera may include one or more filters configured or tuned to block incident light outside a desired range for imaging (typically 500-750 nm wavelength for lipofuscin autofluorescence in retinal AF imaging). For example, the retinal imaging device 104 may be a confocal scanning laser ophthalmoscopy (cSLO) device, as known in the industry. A patient's head may rest on the patient support structure 124 (e.g., chin rest) and an operator may use the control interface 122 (e.g., including joysticks, buttons, touchscreens, displays, etc.) to control the image capture device (e.g., digital camera) and acquire a AF image of the patient's retina. Upon acquisition, the image may be transferred to the computing device 102 via the communication module 126 or stored in a local memory (not shown) for further processing or analysis by a human review.

In some embodiments, the computing device 102 and the retinal imaging device 104 may be communicatively connected such that the retinal imaging device 104 may transfer images to the computing device 102 for analysis according to the processes described below. For example, the computing device 102 and the retinal imaging device 104 may be operatively connected via a wired connection such as a coaxial cable, optical fiber cable, universal serial bus (USB), or twisted pair cable. Alternatively, the computing device 102 and the retinal imaging device 104 may be connected via any suitable wired or wireless network, such as a wireless local area network (WLAN). In some embodiments, additional computing devices (not shown) may receive images from the retinal imaging device 104, store the images, and communicate the images to the computing device 102 for analysis. Additionally, or alternatively, a user may transfer images from the retinal imaging device 104 to the computing device 102 via a removable memory device (not shown). For example, a user may download one or more images from the retinal imaging device 104 onto a removable memory device, such as a flash memory card, and physically connect the removable memory device to the computing device 102 to subsequently upload the images from the removable memory device to the computing device 102. Thus, in some embodiments, a communicative connection 106 between the computing device 102 and the retinal imaging device 104 may be absent.

The computing device 102 may include a memory 108, a central processing unit (CPU) 112, a network interface 118, and a user interface 114. The memory 108 may be implemented as a semiconductor, magnetic, optical, or other type of memory and may include volatile or non-volatile components, which may include removable or non-removable media. The memory 108 may store an automated OD detection routine 110 to perform part or all of the methods described herein, as well as other routines, modules, programs, or applications. The CPU 112 may be adapted and configured to execute various software routines, including the automated OD detection routine 110. When executed by a CPU 112, the software may cause the computing device 102 to receive input from a user via user interface 114 (e.g., including a keyboard, mouse, touchscreen, etc.), communicate with and receive images from the retinal imaging device 104, and automatically evaluate the received images by the automated OD detection routine 110. Further details regarding the automated OD detection routine 110 are discussed below. Although only one memory 108 and one CPU 112 are shown, embodiments of the computing device 102 may include a plurality of memories or CPUs, as well as other components not shown.

In some embodiments, the computing device 102 or the retinal imaging device 104 may store images (e.g., captured AF images of retinas), in an image database 116 communicatively connected to the computing device 102. For example, the image database 116 may store images of a patient's fundus over time, thus allowing the computing device 102 to analyze time elapsed imagery of a patient's fundus. In some cases, the image database 116 may be a remote database that is not physically connected to the computing device 102. For example, the image database 116 may be a network accessible database with which the computing device 102 may communicate via a network interface 118.

Optic Disc Detection

The systems and methods generally described herein may be used to detect an optic disc in a fundus autofluorescence ("AF") image. The AF image may first be processed to correct illumination and contrast irregularities, and segmentation of blood vessels within the image may be performed. In some embodiments, the identified blood vessel segments may be removed from the image to facilitate classification and assessment of the remaining pixels to identify the optic disc. Pixel-wise classification may be used to identify clusters of pixels that may represent an optic disc. Region-wise analysis of the clusters of pixels may then be performed by fitting circles to the clusters and determining blood vessel segments intersecting the circles. Based in part or whole upon the blood vessel segments intersecting the circles, an area containing the optic disc may be detected within the AF image. Once the area of the optic disc is determined, the shape or contours of the optic disc may further be determined.

Figure 3:
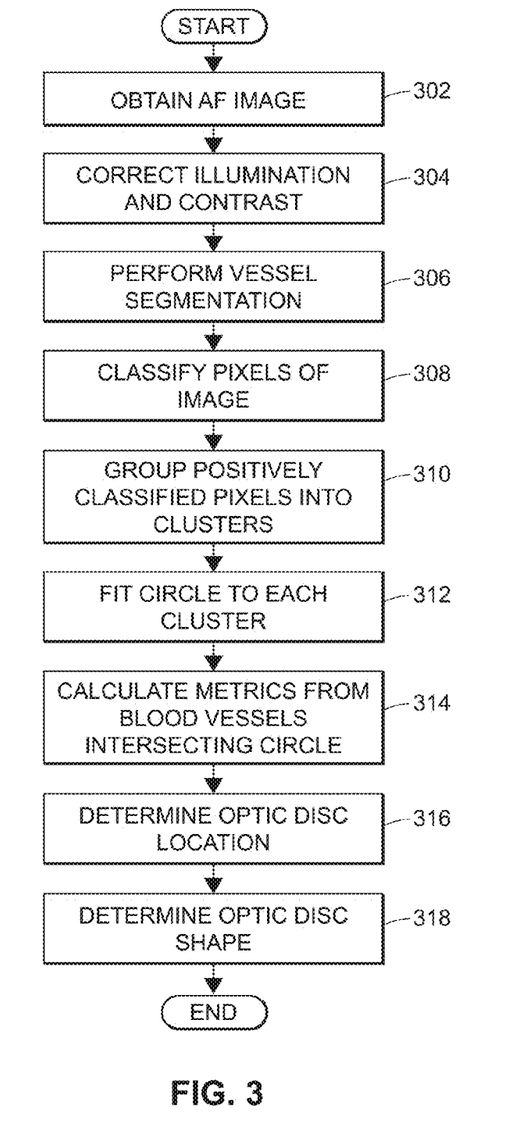
FIG. 3 illustrates a flow diagram of an exemplary method of detecting optic discs in fundus autofluorescence images in accordance with the embodiments described herein.

FIG. 3 illustrates a block diagram of an exemplary optic disc detection method 300. The exemplary method 300 begins by obtaining a AF image at block 302, which may be corrected for uneven illumination and contrast at block 304. Vessel segmentation may be performed on the corrected image at block 306 to identify blood vessels of the retina. Pixels of the corrected image (excluding pixels identified as blood vessels in some embodiments) may be classified at block 308 to identify pixels that may be part of an optic disc. Based upon the classifications, the pixels may be grouped into clusters at block 310. Regions containing identified clusters may then be further analyzed to determine whether they contain an optic disc at blocks 312-316. A best-fit circle or curve may be determined at block 312 for the region of the image in which a cluster was identified. In some embodiments, an expanded circle may be determined from the best-fit circle or curve. Using the circle and the identified blood vessel segments, measures of features associated with optic discs (e.g., radial vessel density, alignment, or thickness) may be calculated at block 314. Whether an optic disc lies within the region under analysis may be determined at block 316 by computer learning techniques from the measures calculated at block 314. The shape of the optic disc may further be determined at block 318 when an optic disc has been located within a region (i.e., when it is determined that a circle contains a representation of the optic disc within the AF image of the retina). The detected optic disc may then be highlighted, measured, or removed to allow further assessment of the retina, as needed.

At block 302, the computing device 102 may receive, retrieve, or otherwise obtain the AF image. In some embodiments, this may include requesting the image from the images database 116. In other embodiments, this may include receiving the image from the retinal imaging device 104. The computing device 102 may further cause the retinal imaging device 104 to capture the image. To capture the image, the retinal imaging device 104 may transmit electromagnetic radiation into the eye to stimulate autofluorescence in the retina. The autofluorescence stimulated by such transmission may pass out of the eye and be received by the image capture device 119. The computing device 102 or the retinal imaging device 104 may then generate a digital image of the retina from the received autofluorescence.

At block 304, the computing device 102 may correct uneven illumination or contrast within the received image. Before carrying out object detection in retinal images, it is often beneficial to correct for any inconsistencies in image illumination, contrast, or other similar features caused by image acquisition variables. In some embodiments, illumination and contrast may be corrected by known techniques that model the image background to account for underlying illumination and contrast drifts. For example, the techniques described in Foracchia et al., "Luminosity and Contrast Normalization in Retinal Images" in Medical Image Analysis, vol. 9, no. 3, p. 179 (2005) and in Cree et al., "The Preprocessing of Retinal Images for the Detection of Fluorescein Leakage" in *Physics in Medicine and Biology*, vol. 44, no. 1, p. 293 (1999) may be used. Such techniques involve recovery of an image $\hat{I}^o$, that represents an original and undistorted image $I^o$ using the equation:

$$\hat{I}^o = \frac{I - \hat{L}}{\hat{C}}$$

where $\hat{L}$ and $\hat{C}$ are estimates of the illumination and contrast drifts, respectively. These estimates may be obtained using an adaptation of a third degree polynomial fitting method, in which a polynomial function is fitted to estimated background points in the image.

In further embodiments, the known techniques may be modified to correct uneven illumination and contrast at block 304 by using two separate polynomials for $\hat{L}$ and $\hat{C}$. The image may be initially partitioned into an M×N grid in order to estimate background pixel intensity using a thresholding of Mahalanobis distances. In a preferred embodiment, a 4×4 grid of rectangular or square partitions may be used. Within each partition, local means and standard deviations may be calculated and used to calculate Mahalanobis distances for each pixel. A quad-tree decomposition may then be used to obtain uniformly sized collections of background pixels over which new local means and standard deviations of pixel intensity may be calculated. These new background mean and standard deviation sample points may be placed at the center of each box in the quad-tree decomposition and further used to fit $\hat{L}$ and $\hat{C}$, respectively. Once estimates of $\hat{L}$ and $\hat{C}$ are determined, illumination and contrast may be corrected in the image. In some embodiments, a new corrected image may be generated, thereby preserving the original image.

At block 306, the computing device 102 may perform vessel segmentation on the corrected image to identify blood vessel segments within the image. The blood vessel segments may be identified by their contrasting intensity against the retina background of the image, as seen in FIG. 2. Although any known method may be used to segment the blood vessels in the image, preferred embodiments include using supervised machine learning with a line operator and oriented Gabor wavelets. Line operators are useful illumination invariant features that respond strongly to linear objects that have some level of noticeable contrast with the image background, which is true for the blood vessels in AF images. This property is similarly exhibited in the case of elongated Gabor wavelets. Thus, linear features of the image with high contrast (such as blood vessels) may be identified using the wavelets or line operator as filters. In some embodiments, elongated Morlet wavelets (real portions of Gabor wavelets) may be used as an approximation of Gabor wavelets.

Elongated Gabor or Morlet wavelets may be convolved with the corrected image to obtain oriented responses as features of pixels within the image. The maximum response over a plurality (e.g., 9, 18, 36) of uniformly distributed rotational orientations may be calculated for each pixel in the image. In some embodiments, responses may be calculated for a plurality of rotational orientations and for a plurality of scales to obtain better results. In a preferred embodiment, 18 rotational orientations ranging from 0 to 180 degrees are calculated as a feature for every pixel of the image for five different scales. In a similar manner, maximum line operator responses may be calculated for a plurality of orientations and scales. In a preferred embodiment, maximum line operator responses are calculated over 12 different orientations in the range of 0 to 180 degrees, and this is repeated at three different scales. The maximum responses from the wavelets and line operators may be stored for further processing, along with the angles at which the maximum responses are observed for the pixels of the image. In a preferred embodiments, texture images of the responses for each orientation and scale may be stored for use both in blood vessel segmentation and for pixel-wise classification and grouping below.

Figure 4:
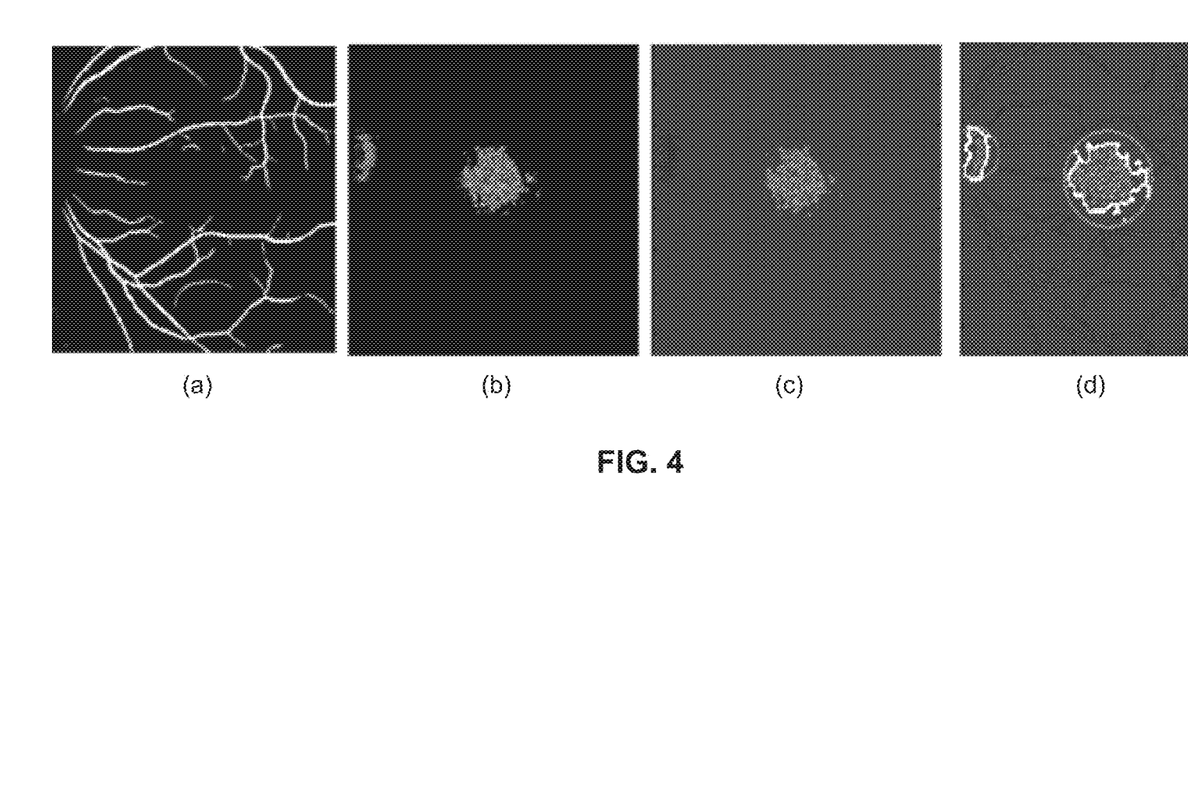
FIG. 4 illustrates exemplary images generated from a fundus autofluorescence image of a retina by the method of FIG. 3.

Once the responses have been obtained, the blood vessels may be segmented. Smoothed intensity may also be used as a feature for segmentation. In some embodiments, machine learning may be used to classify the pixels and identify blood vessel segments. One of the many known learning algorithms, such as support vector machine (SVM), AdaBoost, Naïve Bayes, or neural network algorithms may be used to determine the blood vessel structure in the image. A binary image of the identified blood vessel segments, including the pixels identified as part of blood vessel segments, may be generated and stored for further use. FIG. 4(a) illustrates an exemplary result of the blood vessel segmentation at block 306, showing the blood vessel segments.

At block 308, the computing device 102 may classify pixels of the image. Such classification may identify whether pixels are likely to be associated with an optic disc or the level of likelihood of such association. In some embodiments, pixels associated with the identified blood vessel segments may be excluded from classification or may be classified as not associated with an optic disc. In other embodiments, pixels associated with blood vessel segments may be classified using the same criteria as other pixels. Classification may include pixel-wise feature extraction to identify pixels that may be part of an optic disc within the image. This may be accomplished by determining the degree to which pixels with low intensity (indicating low autofluorescence) are near other pixels with low intensity. As with blood vessel segmentation, elongated Gabor wavelets or elongated Morlet wavelets may be used. Rather than using the oriented responses to determine linear segments, however, the oriented responses may be summed over a plurality of orientations. Summing responses to multiple orientations and scales of the wavelets generates a measure of density of low-intensity pixels (e.g., possible optic disc pixels) in multiple directions from the pixel being considered. Thus, pixels in a cluster of low autofluorescence are classified as being more likely to be part of an optic disc. In some embodiments, this may include determining a probability or value indicating the degree to which the pixel is likely to be part of an optic disc. In further embodiments, this may include a binary classification of pixels as either possible optic disc pixels or not possible optic disc pixels. Such binary classification may be based upon a threshold level applied to a determined probability, intensity, or value.

In a preferred embodiment, classification once again utilizes the elongated Gabor or Morlet wavelets to calculate a series of summed responses over several different orientations and scales, as above. Indeed, efficient processing may be achieved by reusing the same Gabor transform texture images generated and stored above at block 306, thereby reducing use of the CPU 112. Also as above, smoothed intensity may be used in some embodiments. Using the summed responses, the pixels of the image may be classified using machine learning techniques to classify the pixels of the image, such as support vector machine (SVM), AdaBoost, Neve Bayes, or neural network algorithms. In some embodiments, the computer learning techniques may classify pixels as being positively classified if the pixels are sufficiently likely to be associated with an optic disc. This may include determining that the pixels are above a threshold probability. FIG. 4(b) illustrates an exemplary result of the classification at block 306, showing possible optic disc pixels.

At block 310, the computing device 102 may group pixels that were positively classified as possibly indicative of an optic disc into clusters within the image for further analysis. In some embodiments, clusters having fewer than a minimum threshold number of pixels may be excluded to improve processing efficiency. The positively classified pixels may be clustered based upon Euclidian distances in the image using known techniques, such as hierarchical cluster tree or other similar clustering algorithms. In some embodiments, regions may be associated with each identified cluster, such that a finite number of distinct regions are identified, each containing only one cluster of positively classified possible optic disc pixels. FIG. 4(c) illustrates an exemplary result of the clustering at block 306, showing a cluster of grouped pixels in the center.

In blocks 312-316, one or more regions containing the clusters identified at block 310 may be analyzed to determine whether they contain an optic disc. The actions at blocks 312-316 may be performed in a stepwise manner such that each action is performed for each region or in a parallel manner such that each region is analyzed concurrently. Alternatively, the actions at blocks 312-316 may be performed in a sequential manner such that the actions of blocks 312-316 are first performed for a single region, then performed for a different region until all regions have been analyzed. In some embodiments, sequential analysis may end when an optic disc is detected, regardless of whether additional unanalyzed regions remain. This may be done because each eye contains only one optic disc, so each retina image may include at most one optic disc. To improve processing performance, regions containing clusters farther from the center of the image (or nearer to a corner or edge of the image) may be analyzed first as being more likely to contain an optic disc in many applications where retinal imaging is used.

At block 312, the computing device 102 may fit a circle to the positively classified pixels of a region identified as containing a grouped cluster of pixels. The circle may be based upon a best-fit circle, curve, or portion thereof for the pixels. For a distinct region or cluster of pixels identified above, the computing device 102 may fit a circle to the perimeter of the cluster of pixels. This may include fitting a circle that is partially outside the area of the image or region. In such instances, the circle may be fitted to maximize goodness of fit with the pixels for only the portion of the circle within the image or within the region. Thus, a partial circle may be fitted to the cluster of pixels, but the partial circle will be associated with a full circle that extends partially beyond the area of the image or the region under consideration. Any known curve estimation algorithm may be used to fit the circle to the pixels. In some embodiments, this may include determining a best-fit circle from one or more circles. To determine the goodness of fit of the circles, each circle's positive predictive value (ppv) or the rate of false negatives (i.e., positively classified pixels outside the circle) relative to the total area of the circle (fn/total area) may be determined as follows:

$$ppv = \frac{\text{number of OD positive pixels within circle}}{\text{total number of pixels within circle}}$$

$$fn/\text{total area} = \frac{\text{number of OD positive pixels outside circle}}{\text{total number of pixels within circle}}$$

The best-fit circle may then be determined based upon these metrics of goodness of fit. In some embodiments, the best fit circle may be used to further determine an expanded circle for use in further analysis to determine the location of the optic disc. Because image contrast is sometimes poor around the periphery of the optic disc, the expanded circle may instead be used for further analysis. In preferred embodiments, the expanded circle is concentric with the best-fit circle and will has radius from a quarter to a half larger than the radius of the best-fit circle. In a particularly preferred embodiment, the radius of the expanded circle is approximately one third (such as 30%, 33%, or 35%) larger than the radius of the best-fit circle. FIG. 4(d) illustrates an exemplary image showing the expanded circles around two clusters.

At block 314, the computing device 102 may calculate one or more measures associated with the blood vessel segments intersecting the circle determined at block 312. Measures of radial vessel density, alignment, or thickness may be determined for blood vessel segments intersecting the circle. In some embodiments, processing efficiency of the computing device 102 may be improved by using the line operator responses determined at block 306 to determine the alignment or orientation of the blood vessel segments without recalculating the orientation of the blood vessel segments within the image. As noted above, either a best-fit circle or an expanded circle may be used to calculate the one or more measures. Although certain metrics are discussed in detail below, other metrics based upon the blood vessel segments intersecting the circle may be used in various additional embodiments.

The first vessel-derived metric is a measure of radial vessel density. A measure of blood vessel segments intersecting the circle may be calculated. In some embodiments, the measure may include a summation of the number of blood vessel segment pixels that make contact with the circle. Thus, blood vessel segments that are thicker at the point of intersection with the circle are weighted more heavily by the number of their pixels that contain a portion of the circle (which may include a point of the circle at an edge or corner of the pixel). The blood vessel segment pixels that contact the circle may be determined using the blood vessel pixels from the binary image or other information determined during blood vessel segmentation, as discussed above. In some embodiments, each intersecting blood vessel pixel may be weighted by its alignment to the radial direction of the circle at the pixel, and the weighted pixels may be summed. The angle of the maximum line operator strength at that pixel determined above during vessel segmentation may be used as the measure of the orientation of the blood vessel segment pixel ($\theta_{vessel}$), which improves processing efficiency. The radial direction of the circle at the pixel ($\theta_{circle}$) may be determined as the orientation of a line drawn through the center of the circle arc within the pixel in the radial direction to that point from the centroid of the circle. Each blood vessel segment pixel that contacts the circle may thus be weighted by its alignment weight, defined as follows:

$$\text{alignment weight} = 1 - \frac{|\theta_{vessel} - \theta_{circle}|}{90}$$

Using this weighting equation gives weighting values from 0 to 1, where 0 is the weight given if the blood vessel pixel has an orientation tangent to the circle and 1 is the weight given if the blood vessel pixel is perfectly aligned with the radius of the circle at the point of contact. This weighting takes into account the expectation that vessels surrounding the optic disc should be approximately normal to the perimeter of the optic disc, which is estimated by the circle. Similarly, the optic disc should have a high number of normal vessel pixels at the circle perimeter, which is captured by the summation of the weighted pixels. In further embodiments, the weighted (or unweighted) sum of the intersecting blood vessel segment pixels may be normalized for the length of the portion of the circle lying within the image or region under consideration. The measure may thereby account for optic discs lying partially off the frame, which would be expected to have proportionally fewer blood vessel segment intersections within the image or region than an optic disc lying entirely within the image or region. Normalization may be performed by dividing the weighted vessel pixel count by a count of pixels that comprise the circle border within the image or region under consideration. This metric is useful in determining whether the circle contains an optic disc because more and larger blood vessel segments with more radial orientations are expected to be found emanating from a circle containing an optic disc.

Another vessel-derived metric is a measure of the average alignment of blood vessel segment pixels. This may be measured by averaging the alignment of the pixels of blood vessel segments contacting the circle to the radial direction of the circle at the pixel, as discussed above. In some embodiments, the alignment of blood vessel segment pixels may include blood vessel pixels within the circle, either in addition to those contacting the circle or as an alternative to those contacting the circle. For interior pixels, the alignment may be measured as a difference between the orientation of the pixel and the orientation of a radial line from the centroid of the circle through the interior pixel (e.g., through the center of the pixel). This metric is useful in determining whether the circle contains an optic disc because more radial orientations of blood vessels segments are expected for a circle containing an optic disc.

Another vessel-derived metric is a measure of the density of blood vessel crossings of the circle. This may be measured by skeletonizing the blood vessel segments to eliminate the effect of thickness of blood vessels intersecting the circle. The measure of the density of blood vessel crossings may then be calculated as the sum of all skeletonized blood vessels segments that intersect the circle. In some embodiments, the measure may further be normalized by the length of the portion of the circle lying within the image or region under consideration, such as by dividing the sum of the skeletonized blood vessel segments that intersect the circle by the length of the arc of the circle within the image or region under consideration. This metric is useful in determining whether the circle contains an optic disc because more crossings are expected for a circle containing an optic disc, as all major blood vessels reach the retina via the optic disc.

Another vessel-derived metric is a measure of the normalized size of the possible optic disc pixel cluster. This may be measured as the radius of the circle divided by the average blood vessel thickness in the image. In some embodiments, the average blood vessel thickness may be determined by dividing the total number of blood vessel pixels in the image or in a region of the image by the total number of skeletonized blood vessel pixels in the image or region of the image.

At block 316, the computing device 102 may determine whether the circle or region under consideration contains the optic disc based upon the measures calculated at block 314. Using the above-described or similar metrics, the cluster or region may be classified using a machine learning technique, such as support vector machine (SVM), AdaBoost, Naïve Bayes, or neural network algorithms. For example, one or more probabilities of a cluster being an optic disc may be generated in the classification process. The probabilities may then be compared against a threshold level (e.g., 0.85, 0.90, 0.95) to determine whether the circle or region contains an optic disc. In a preferred embodiment, the threshold level is set to a probability of 0.90 that the circle contains the optic disc. Also in a preferred embodiment, the method 300 terminates when a cluster is determined to exceed the probability threshold. Because AF images typically will not include sufficient detail within the optic disc to differentiate blood vessels within optic discs, it is advantageous that the metrics above ignore the blood vessels within the possible optic disc. Thus, in preferred embodiments, the computing device 102 will determine the circle or region contains the optic disc without including any analysis of any aspects of the structure or presence of blood vessels within the optic disc (i.e., within the possible optic disc pixels of the cluster under consideration).

When an optic disc is located within any of the regions analyzed in blocks 312-316, the region may be further analyzed to determine the specific location and shape of the optic disc. At block 318, the computing device 102 may determine the shape or contours of the optic disc based upon the classified pixels of the image within the region. In some embodiments, the texture images generated and stored above may be used to determine the shape of the optic disc. For example, a rectangular section may be cropped from the corrected image and from the generated texture images, which cropped portions of the images may be combined into an image having multi-dimensional pixels. The multi-dimensional pixels may include information regarding the corrected intensity of the pixels, the maximum responses of the pixels to the wavelet filters, the maximum responses of the pixels to the line operator filters, the classification of the pixels as blood vessel segment pixels, or the classification of the pixels as possible optic disc pixels. A level-set algorithm for vector-valued images may be run on the multi-dimensional pixels of the combined image to determine the outline, boundary, or shape of the optic disc. For example, the algorithms described in Chan et al., "Active Contours without Edges for Vector-Valued Images" in *Journal of Visual Communication and Image Representation*, vol. 11, no. 2, p. 130 (2000) may be used. This may generate a more accurate outline of the optic disc based on region-wise consistency in texture and intensity than would the initial pixel-wise classification of pixels as being possible optic disc pixels that was used to generate the initial cluster. Because the existing texture image information is used, this method reduces processor usage improves processing efficiency, as well as memory usage because additional intermediate images need not be stored.

Figure 5:
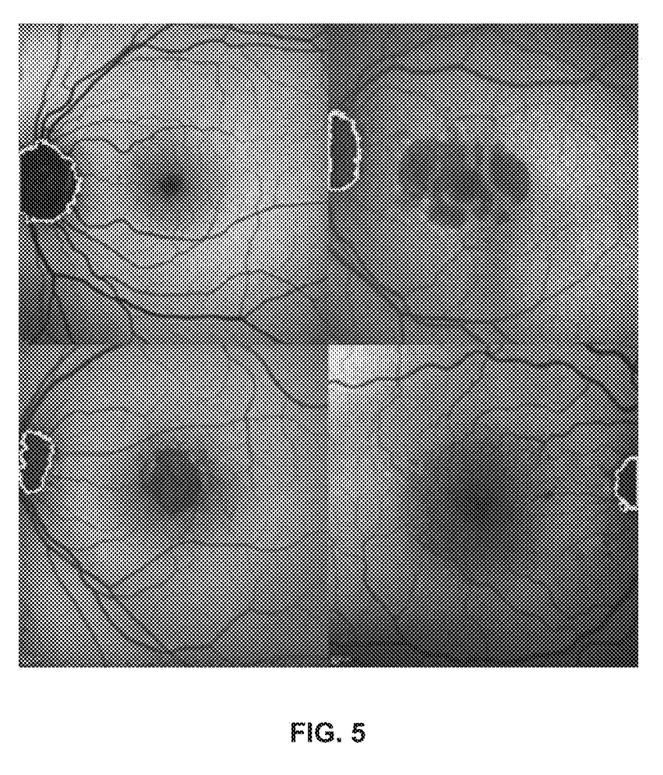
FIG. 5 illustrates exemplary fundus autofluorescence images of a retina showing the optic discs detected by the method of FIG. 3.

Once the location and shape of the optic disc has been detected by the optic disc detection method 300, information regarding the detected optic disc may be stored or presented to a user of the computing device 102. FIG. 5 illustrates exemplary AF images of a retina showing the outlines of detected optic discs. As illustrated therein, the optic discs can be distinguished from other clusters of dark pixels within the image, even when the optic disc lies partially beyond the edge of the image. Such images may be used to further assess retinal health of a patient through analysis of the macula or by comparison of optic disc size, shape, or regularity. As may be seen in the exemplary images, the methods described herein enable detection of the optic disc even where blood vessels within the optic disc cannot be identified or analyzed. This is of particular use in AF images, where such information regarding blood vessels within the optic disc is typically unavailable. The methods and systems described herein are not limited to AF images, however, and may be used with other types of retinal images (particularly with monochromatic images).

Additional Considerations

Upon reading this disclosure, those of ordinary skill in the art will appreciate still additional alternative structural and functional designs for automatically detecting optic discs. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention. By way of example, and not limitation, the present disclosure contemplates at least the following aspects:

1. A computer-implemented method for automatically identifying optic discs, the method comprising: receiving, at one or more processors, a fundus autofluorescence image of an ocular fundus; identifying, by one or more processors, blood vessel segments within the received image; classifying, by one or more processors, a plurality of pixels of the image as possible optic disc pixels; identifying, by one or more processors, a group of possible optic disc pixels; fitting, by one or more processors, at least a portion of a circle to the group of possible optic disc pixels; identifying, by one or more processors, each of the blood vessel segments that intersects the circle; weighting, by one or more processors, each intersecting blood vessel segment based upon its alignment to the radial direction of the circle at the point of intersection; calculating, by one or more processors, a measure of radial vessel density based upon the weighted blood vessel segments and the length of the portion of the circle; determining, by one or more processors, whether the circle contains the optic disc based at least in part upon the measure of radial vessel density; and determining, by one or more processors, the boundaries of the determined optic disc based at least in part upon the possible optic disc pixels within the circle when the circle is determined to contain the optic disc.

2. The computer-implemented method according to aspect 1, wherein fitting the at least a portion of a circle to the group of possible optic disc pixels includes: determining a best fit circle; determining an expanded circle concentric with the best fit circle that has a radius larger than the radius of the best fit circle; and determining the portion of the expanded circle that lies within the received image.

3. The computer-implemented method according to either of aspect 1 or aspect 2, wherein the radius of the expanded circle is between 25% and 50% larger than the radius of the best fit circle.

4. The computer-implemented method according to any one of aspects 1-3, further comprising: generating, by one or more processors, an illumination corrected image by correcting uneven illumination and contrast in the received image; generating, by one or more processors, a texture image by filtering the received image using filters that emphasize blood vessels; determining, by one or more processors, corresponding regions of each of the received image, the illumination corrected image, and the texture image, wherein: each of the corresponding regions represents the same area of the fundus in the received image, and the corresponding regions contain the portion of the circle that is within each image; and generating, by one or more processors, a combined image comprising multi-dimensional pixels by combining the received image, the illumination corrected image, and the texture image, and wherein determining the boundaries of the determined optic disc includes determining the boundaries based upon the multi-dimensional pixels of the combined image.

5. The computer-implemented method according to any one of aspects 1-4, wherein receiving the fundus autofluorescence image includes: transmitting, from a light source of a camera, a stimulating light into the retina; receiving, at an optical sensor of the camera, autofluorescence from the ocular fundus; and processing, by one or more processors, the received autofluorescence into a monochromatic digital image.

6. The computer-implemented method according to any one of aspects 1-5, wherein determining whether the circle contains the optic disc is further based upon one or more of the following measures: a measure of alignment of the intersecting blood vessel segments, which measures the average alignment to the radial direction of the circle at the point of intersection of each intersecting blood vessel segment; a measure of the density of blood vessel crossings, which measures the number of intersecting blood vessel segments relative to the length of the circumference of the portion of the circle within the image; or a measure of normalized size of the group of possible optic disc pixels, which measures the radius of the circle divided by an average thickness of blood vessels within the image.

7. The computer-implemented method according to any one of aspects 1-6, wherein fitting that at least a portion of the circle to the group of possible optic disc pixels includes: using a curve estimation algorithm to generate one or more potential circles around the perimeter of the group of possible optic disc pixels; determining a measure of the goodness of fit of each of the one or more potential circles; and selecting the potential circle with the best measure of the goodness of fit.

8. The computer-implemented method according to any one of aspects 1-7, wherein determining whether the circle contains the optic disc does not include analyzing one or more aspects of the structure of blood vessels within the optic disc.

9. The computer-implemented method according to any one of aspects 1-8, wherein determining whether the circle contains the optic disc includes: determining a probability that the circle contains the optic disc using a machine learning process; and determining the circle contains the optic disc when the determined probability exceeds a threshold level.

10. The computer-implemented method according to any one of aspects 1-9, wherein: a plurality of groups of possible optic disc pixels are identified; a measure of radial vessel density is calculated for each identified group; and only one group is determined to the optic disc based at least in part upon the measure of radial vessel density.

11. A computer system for automatically identifying optic discs, comprising: one or more processors; and one or more memories coupled to the one or more processors, wherein the one or more memories store computer executable instructions that, when executed by the one or more processors, cause the one or more processors to: receive a fundus autofluorescence image of an ocular fundus; identify blood vessel segments within the received image; classify a plurality of pixels of the image as possible optic disc pixels; identify a group of possible optic disc pixels; fit at least a portion of a circle to the group of possible optic disc pixels; identify each of the blood vessel segments that intersects the circle; weight each intersecting blood vessel segment based upon its alignment to the radial direction of the circle at the point of intersection; calculate a measure of radial vessel density based upon the weighted blood vessel segments and the length of the portion of the circle; determine whether the circle contains the optic disc based at least in part upon the measure of radial vessel density; and determine the boundaries of the determined optic disc based at least in part upon the possible optic disc pixels within the circle when the circle is determined to contain the optic disc.

12. The computer system according to aspect 11, wherein the executable instructions that cause the computer to fit the at least a portion of a circle to the group of possible optic disc pixels further cause the computer to: determine a best fit circle; determine an expanded circle concentric with the best fit circle that has a radius larger than the radius of the best fit circle; and determine the portion of the expanded circle that lies within the received image.

13. The computer system according to either of aspect 11 or aspect 12, wherein the executable instructions further cause the computer system to: generate an illumination corrected image by correcting uneven illumination and contrast in the received image; generate a texture image by filtering the received image using filters that emphasize blood vessels; determine corresponding regions of each of the received image, the illumination corrected image, and the texture image, wherein: each of the corresponding regions represents the same area of the fundus in the received image, and the corresponding regions contain the portion of the circle that is within each image; and generate a combined image comprising multi-dimensional pixels by combining the received image, the illumination corrected image, and the texture image, and wherein determining the boundaries of the determined optic disc includes determining the boundaries based upon the multi-dimensional pixels of the combined image.

14. The computer system according to any one of aspects 11-13, wherein the one or more memories do not store computer executable instructions that cause the computer system to analyze one or more aspects of the structure of blood vessels within the optic disc.

15. A tangible, non-transitory computer-readable medium storing executable instructions for automatically identifying optic discs that, when executed by one or more processors of a computer system, cause the computer system to: receive a fundus autofluorescence image of an ocular fundus; identify blood vessel segments within the received image; classify a plurality of pixels of the image as possible optic disc pixels; identify a group of possible optic disc pixels; fit at least a portion of a circle to the group of possible optic disc pixels; identify each of the blood vessel segments that intersects the circle; weight each intersecting blood vessel segment based upon its alignment to the radial direction of the circle at the point of intersection; calculate a measure of radial vessel density based upon the weighted blood vessel segments and the length of the portion of the circle; determine the circle contains the optic disc based at least in part upon the measure of radial vessel density; and determine the boundaries of the determined optic disc based at least in part upon the possible optic disc pixels within the circle.

16. The tangible, non-transitory computer-readable medium according to aspect 15, wherein the executable instructions that cause the computer to fit the at least a portion of a circle to the group of possible optic disc pixels further cause the computer to: determine a best fit circle; determine an expanded circle concentric with the best fit circle that has a radius larger than the radius of the best fit circle; and determine the portion of the expanded circle that lies within the received image.

17. The tangible, non-transitory computer-readable medium according to either of aspect 15 or aspect 16, further comprising executable instructions that cause the computer system to: generate an illumination corrected image by correcting uneven illumination and contrast in the received image; generate a texture image by filtering the received image using filters that emphasize blood vessels; determine corresponding regions of each of the received image, the illumination corrected image, and the texture image, wherein: each of the corresponding regions represents the same area of the fundus in the received image, and the corresponding regions contain the portion of the circle that is within each image; and generate a combined image comprising multi-dimensional pixels by combining the received image, the illumination corrected image, and the texture image, and wherein determining the boundaries of the determined optic disc includes determining the boundaries based upon the multi-dimensional pixels of the combined image.

18. The tangible, non-transitory computer-readable medium according to any one of aspects 15-17, wherein the executable instructions do not cause the computer to analyze the structure of blood vessels within the optic disc.

19. The tangible, non-transitory computer-readable medium according to any of aspects 15-18, wherein the executable instructions that cause the computer system to determine whether the circle contains the optic disc further cause the computer system to determine the circle contains the optic disc based in part upon one or more of the following measures: a measure of alignment of the intersecting blood vessel segments, which measures the average alignment to the radial direction of the circle at the point of intersection of each intersecting blood vessel segment; a measure of the density of blood vessel crossings, which measures the number of intersecting blood vessel segments relative to the length of the circumference of the portion of the circle within the image; or a measure of normalized size of the group of possible optic disc pixels, which measures the radius of the circle divided by an average thickness of blood vessels within the image.

20. The tangible, non-transitory computer-readable medium according to any one of aspects 15-19, wherein the executable instructions that cause the computer system to determine whether the circle contains the optic disc include instructions that cause the computer system to: determine a probability that the circle contains the optic disc using a machine learning process; and determine the circle contains the optic disc when the determined probability exceeds a threshold level.

What is claimed is:

1. A computer-implemented method for automatically identifying optic discs in fundus autofluorescence images, the method comprising:
   receiving, at one or more processors, a fundus autofluorescence image of an ocular fundus;
   identifying, by one or more processors, blood vessel segments within the received image based upon indications of light intensity of pixels associated with the identified blood vessel segments within the received image;
   classifying, by one or more processors, a plurality of pixels of the image as being possible optic disc pixels based at least in part upon determined features of each of the plurality of pixels;
   identifying, by one or more processors, a group of possible optic disc pixels based at least in part upon proximity of a plurality of possible optic disc pixels within the group of possible optic disc pixels;
   fitting, by one or more processors, at least a portion of a circle to the group of possible optic disc pixels;
   identifying, by one or more processors, each of the blood vessel segments that intersects the circle;
   weighting, by one or more processors, each intersecting blood vessel segment based upon its alignment to a radial direction of the circle at a point of intersection of the intersecting blood vessel segment and the circle;
   calculating, by one or more processors, a measure of radial vessel density based upon the weighted blood vessel segments and the length of the portion of the circle;
   determining, by one or more processors, whether the circle contains an optic disc based at least in part upon the measure of radial vessel density; and
   determining, by one or more processors, the boundaries of the determined optic disc based at least in part upon the possible optic disc pixels within the circle when the circle is determined to contain the optic disc.

2. The computer-implemented method of claim 1, wherein fitting the at least a portion of a circle to the group of possible optic disc pixels includes:
   determining a best fit circle;
   determining an expanded circle concentric with the best fit circle that has a radius larger than the radius of the best fit circle; and
   determining the portion of the expanded circle that lies within the received image.

3. The computer-implemented method of claim 2, wherein the radius of the expanded circle is between 25% and 50% larger than the radius of the best fit circle.

4. The computer-implemented method of claim 1, further comprising:
   generating, by one or more processors, an illumination corrected image by correcting uneven illumination and contrast in the received image;
   generating, by one or more processors, a texture image by filtering the received image using filters that emphasize blood vessels;
   determining, by one or more processors, corresponding regions of each of the received image, the illumination corrected image, and the texture image, wherein:
      each of the corresponding regions represents the same area of the ocular fundus in the received image, and
      the corresponding regions contain the portion of the circle that is within each image; and
   generating, by one or more processors, a combined image comprising multi-dimensional pixels by combining the received image, the illumination corrected image, and the texture image,
   and wherein determining the boundaries of the determined optic disc includes determining the boundaries based upon the multi-dimensional pixels of the combined image.

5. The computer-implemented method of claim 1, wherein receiving the fundus autofluorescence image includes:
   transmitting, from a light source of a camera, a stimulating light into the retina;
   receiving, at an optical sensor of the camera, autofluorescence from the ocular fundus; and
   processing, by one or more processors, the received autofluorescence into a monochromatic digital image.

6. The computer-implemented method of claim 1, wherein determining whether the circle contains the optic disc is further based upon one or more of the following measures:
   a measure of alignment of the intersecting blood vessel segments, which measures average alignment to the radial direction of the circle at the point of intersection of each intersecting blood vessel segment;
   a measure of the density of blood vessel crossings, which measures a number of intersecting blood vessel segments relative to a length of the circumference of the portion of the circle within the image; or
   a measure of normalized size of the group of possible optic disc pixels, which measures the radius of the circle divided by an average thickness of blood vessels within the image.

7. The computer-implemented method of claim 1, wherein fitting the at least a portion of the circle to the group of possible optic disc pixels includes:
   using a curve estimation algorithm to generate one or more potential circles around the perimeter of the group of possible optic disc pixels;
   determining a measure of goodness of fit of each of the one or more potential circles; and
   selecting the potential circle with a best measure of the goodness of fit.

8. The computer-implemented method of claim 1, wherein determining whether the circle contains the optic disc does not include analyzing one or more aspects of the structure of blood vessels within the optic disc.

9. The computer-implemented method of claim 1, wherein determining whether the circle contains the optic disc includes:
   determining a probability that the circle contains the optic disc using a machine learning process; and
   determining the circle contains the optic disc when the determined probability exceeds a threshold level.

10. The computer-implemented method of claim 1, wherein:
   a plurality of groups of possible optic disc pixels are identified;
   a measure of radial vessel density is calculated for each identified group; and
   only one group is determined to contain the optic disc based at least in part upon the measure of radial vessel density.

11. A computer system for automatically identifying optic discs in fundus autofluorescence images, comprising:
   one or more processors; and
   one or more memories coupled to the one or more processors;
   wherein the one or more memories store computer executable instructions that, when executed by the one or more processors, cause the one or more processors to:
      receive a fundus autofluorescence image of an ocular fundus;
      identify blood vessel segments within the received image based upon indications of light intensity of pixels associated with the identified blood vessel segments within the received image;
      classify a plurality of pixels of the image as being possible optic disc pixels based at least in part upon determined features of each of the plurality of pixels;
      identify a group of possible optic disc pixels based at least in part upon proximity of a plurality of possible optic disc pixels within the group of possible optic disc pixels;
      fit at least a portion of a circle to the group of possible optic disc pixels;
      identify each of the blood vessel segments that intersects the circle;
      weight each intersecting blood vessel segment based upon its alignment to a radial direction of the circle at a point of intersection of the intersecting blood vessel segment and the circle;
      calculate a measure of radial vessel density based upon the weighted blood vessel segments and the length of the portion of the circle;
      determine whether the circle contains an optic disc based at least in part upon the measure of radial vessel density; and
      determine the boundaries of the determined optic disc based at least in part upon the possible optic disc pixels within the circle when the circle is determined to contain the optic disc.

12. The computer system of claim 11, wherein the executable instructions that cause the computer to fit the at least a portion of a circle to the group of possible optic disc pixels further cause the computer to:
   determine a best fit circle;
   determine an expanded circle concentric with the best fit circle that has a radius larger than the radius of the best fit circle; and
   determine the portion of the expanded circle that lies within the received image.

13. The computer system of claim 11, wherein the executable instructions further cause the computer system to:

generate an illumination corrected image by correcting uneven illumination and contrast in the received image;

generate a texture image by filtering the received image using filters that emphasize blood vessels;

determine corresponding regions of each of the received image, the illumination corrected image, and the texture image, wherein:

each of the corresponding regions represents the same area of the ocular fundus in the received image, and the corresponding regions contain the portion of the circle that is within each image; and generate a combined image comprising multi-dimensional pixels by combining the received image, the illumination corrected image, and the texture image, and wherein determining the boundaries of the determined optic disc includes determining the boundaries based upon the multi-dimensional pixels of the combined image.

14. The computer system of claim 11, wherein the one or more memories do not store computer executable instructions that cause the computer system to analyze one or more aspects of the structure of blood vessels within the optic disc.

15. A tangible, non-transitory computer-readable medium storing executable instructions for automatically identifying optic discs in fundus autofluorescence images that, when executed by one or more processors of a computer system, cause the computer system to:

receive a fundus autofluorescence image of an ocular fundus;

identify blood vessel segments within the received image based upon indications of light intensity of pixels associated with the identified blood vessel segments within the received image;

classify a plurality of pixels of the image as being possible optic disc pixels based at least in part upon determined features of each of the plurality of pixels;

identify a group of possible optic disc pixels based at least in part upon proximity of a plurality of possible optic disc pixels within the group of possible optic disc pixels;

fit at least a portion of a circle to the group of possible optic disc pixels;

identify each of the blood vessel segments that intersects the circle;

weight each intersecting blood vessel segment based upon its alignment to a radial direction of the circle at a point of intersection of the intersecting blood vessel segment and the circle;

calculate a measure of radial vessel density based upon the weighted blood vessel segments and the length of the portion of the circle;

determine whether the circle contains an optic disc based at least in part upon the measure of radial vessel density; and determine the boundaries of the determined optic disc based at least in part upon the possible optic disc pixels within the circle when the circle is determined to contain the optic disc.

16. The tangible, non-transitory computer-readable medium of claim 15, wherein the executable instructions that cause the computer to fit the at least a portion of a circle to the group of possible optic disc pixels further cause the computer to:

determine a best fit circle;

determine an expanded circle concentric with the best fit circle that has a radius larger than the radius of the best fit circle; and determine the portion of the expanded circle that lies within the received image.

17. The tangible, non-transitory computer-readable medium of claim 15, further comprising executable instructions that cause the computer system to:

generate an illumination corrected image by correcting uneven illumination and contrast in the received image;

generate a texture image by filtering the received image using filters that emphasize blood vessels;

determine corresponding regions of each of the received image, the illumination corrected image, and the texture image, wherein:

each of the corresponding regions represents the same area of the ocular fundus in the received image, and the corresponding regions contain the portion of the circle that is within each image; and generate a combined image comprising multi-dimensional pixels by combining the received image, the illumination corrected image, and the texture image, and wherein determining the boundaries of the determined optic disc includes determining the boundaries based upon the multi-dimensional pixels of the combined image.

18. The tangible, non-transitory computer-readable medium of claim 15, wherein the executable instructions do not cause the computer to analyze the structure of blood vessels within the optic disc.

19. The tangible, non-transitory computer-readable medium of claim 15, wherein the executable instructions that cause the computer system to determine whether the circle contains the optic disc further cause the computer system to determine the circle contains the optic disc based in part upon one or more of the following measures:

a measure of alignment of the intersecting blood vessel segments, which measures average alignment to the radial direction of the circle at the point of intersection of each intersecting blood vessel segment;

a measure of the density of blood vessel crossings, which measures a number of intersecting blood vessel segments relative to a length of the circumference of the portion of the circle within the image; or a measure of normalized size of the group of possible optic disc pixels, which measures the radius of the circle divided by an average thickness of blood vessels within the image.

20. The tangible, non-transitory computer-readable medium of claim 15, wherein the executable instructions that cause the computer system to determine whether the circle contains the optic disc include instructions that cause the computer system to:

determine a probability that the circle contains the optic disc using a machine learning process; and determine the circle contains the optic disc when the determined probability exceeds a threshold level.

* * * * *